United States Patent [19]

Kwon

[11] Patent Number: 4,898,814

[45] Date of Patent: Feb. 6, 1990

[54] A CDNA CLONE FOR HUMAN TYROSINASE

[75] Inventor: Byoung S. Kwon, Vestal, N.Y.

[73] Assignee: Donald Guthrie Foundation for Medical Research, Inc., Sayre, Pa.

[21] Appl. No.: 915,753

[22] Filed: Oct. 6, 1986

[51] Int. Cl.⁴ .................. C12Q 1/68; C12N 9/02; C12N 15/00; C07H 15/12

[52] U.S. Cl. ........................ 435/6; 435/189; 435/172.3; 435/235; 435/320; 536/27; 935/14; 935/31; 935/78

[58] Field of Search .............. 435/6, 172.3, 235, 320, 435/108, 189; 536/27

[56] References Cited

PUBLICATIONS

Gaulton et al., Journal of Biological Chemistry, 258:14845–14849, 1983.
Shibahara et al., Nucleic Acids Research, 14:2413–2427, 1986 (Mar.).
Coleman, D. E. (1962), Arch. Biochem. Biophys. 69, 562–568.
Gluecksohn-Waelsch, S. (1979), Cell, 16, 225–237.
Green, M. C. (1961), Journal of Heredity, 52, 73–75.
Kidson, S. H. & Fabian, B. C.-(1981)-Journal of Exp. Zoology, 215, 91–97.
Halaban, R. & Alfano, F. D.-(1984)-In Vitro, 20, 447–450.
Halaban, R., Ghosh, S., Duray, P., Kirkwood, J. M. & Lerner, A. B.-(1986)-Journal of Investigative Dermatology, 87, 95–101.
Ross, R. A. & Biedler, J. L.-(1985)-Advances in Neuroblastoma, pp. 249–259.
Chirgwin, J. M., Przybyla, A. E., MacDonald, R. J. & Rutter, W. J.-(1979)-Biochemistry, 18, 5294–5299.
Aviv, H. & Leder, P.-(1972)-Proc. Natl. Acad. Sci., USA, 69, 1408–1412.
Biossy, R. E., Moellmann, G. E. & Halaban, R.-(1986)-Journal of Investigative Dermatology, 88, 292–300.
Thomas, P. S.-(1980)-Proc. Natl. Acad. Sci., USA, 77, 5201–5205.
Grass-Bellard, M., Oudet, P. & Chambon, P.-(1973)--Eur. J. Biochem., 36, 32–38.
Southern, E. M.-(1975)-J. Mol. Biol., 98, 503–517.
Sanger, F., Nicklen, S. & Coulson, A. R.-(1977)-Proc. Natl. Acad. Sci., USA, 74, 5463–5467.
Biggin, M., Gibson, T. & Hung, G.-(1983)-Proc. Natl. Acad. Sci., USA, 80, 3963–3965.
Goeddel, D. V., Leung, D. W., Dull, T. J., Gross, M., Lawn, R. M., McCandliss, R., Seeburg, P. H., Ullrich, A., Yelverton, E. & Gray, P. W.-(1981)-Nature (London), 290, 20–26.
Shibahara, S., Tomita, Y., Sakakura, T., Nager, C., Chaudhuri, B. & Muller, R.-(1986)-Nucleic Acids Res., 14, 2413–2427.

(List continued on next page.)

Primary Examiner—Thomas D. Mays
Attorney, Agent, or Firm—Ralph R. Barnard

[57] ABSTRACT

This discovery resulted when a λ gt11 cDNA library of normal human melanocytes were screened with antibodies directed against purified hamster tyrosinase. Sixteen independent clones which gave a positive signal were isolated from $5 \times 10^5$ independent plaques. cDNA inserts of 13 clones among the 16 candidates cross-hybridized with each other, indicating that they were from related mRNA species. mRNA homologous to a representative cDNA λ mel 34 was expressed specifically in melanocytes, detecting an approximately 2.4 kb mRNA species of human melanocytes. The nucleotide sequence of the three overlapping cDNA inserts spanning 1.88 kb was determined and an amino acid sequence was deducted. The human tyrosinase is composed of 548 amino acids with a molecular weight of 62,160 excluding a hydrophobic signal peptide. Mouse genomic DNA blot analysis revealed that the gene for λ mel 34 was deleted in albino mouse homozygous for the deletion at and around the albino locus on chromosome 7. It is concluded that λ mel 34 contained cDNA encoding human tyrosinase. Moreover, the cDNA gene for human tyrosinase was recovered from the λ mel 34 and can be used for many purposes including the production of pure human tyrosinase.

6 Claims, 7 Drawing Sheets

U.S. PATENT DOCUMENTS

Steiner, D. F., Quinn, P. S., Chan, S. J., Marsh, J. & Tager, H. S.-(1980)-Ann. N.Y. Acad. Sci., 343, 1–16.

Marshall, R. D.-(1974)-Biochem. Soc. Symp., 40, 17–26.

Richardson, J. S., Thomas, K. A., Rubin, B. H. & Richardson, D. C.-(1975)-Proc. Natl. Acad. Sci., USA, 72, 1349–1353.

Mason, H. S.-(1948)-J. Biol. Chem., 172, 83–99.

Witkop, C. J., Jr.-(1984)-The Clinics in Dermatology, vol. 2, 70–134.

Halaban, R., Pomerantz, S. H., Marshall, S., Lambert, D. T. & Lerner, A. B.-(1983)-J. Cell. Biol., 97, 480–488.

Land, H., Grez, M., Hauser, H., Lindenmaier, W. & Schutz, G.-(1981)-Nucleic Acids Res. 9, 2251–2261.

Kwon, B. S., Kim, G. S., Prystowsky, M. B., Lancki, D. W., Sabath, D. E., Pan, J. & Weissman, S. M.-(1987)-Proc. Natl. Acad. Sci., USA, 84, 2896–2900.

Young, R. A. & Davis, R. W.-(1983)-Proc. Natl. Acad. Sci., USA, 80, 1194–1198.

Mehra, V., Sweetser, D. & Young, R. A.-(1986)-Proc. Natl. Acad. Sci., USA, 83, 7013–7017.

Blobel, G. & Dobberstein, B.-(1975)-J. Cell. Biol., 67, 852–862.

Bause, E.-(1983)-Biochem. J., 209, 331–336.

Nishioka, K.-(1978)-Eur. J. Biochem., 85, 137–146.

Lerch, D.-(1976)-FEBS Lett., 69, 161–164.

Shibahara, S.-(1987)-Advances in Pigment Cell Research, pp. 263–271.

Yamamoto, H., Takeuchi, S., Kudo, T., Makino, K., Nakata, A., Shinoda, T. & Takeuchi, T.-(1987)-Jpn. J. Genet., 62, 271–274.

Messing, J., Crea, R. & Seeburg, P. H.-(1981)-Nucleic Acids Res., 9, 309–322.

```
      -40              -30              -20              -10           -1  1                10
GAA TTC CTG CTC CTG GCT GTT TTG TAC TGC CTG CTG TGG AGT TTC CAG ACC TCC GCT GGC
------------ Leu Leu Leu Ala Val Leu Tyr Cys Leu Leu Trp Ser Phe Gln Thr Ser Ala Gly
EcoRI                 -10                                            -1   1

20              30              40              50              60              70
CAT TTC CCT AGA GCC TGT GTC TCC TCT AAG AAC CTG ATG GAG AAG GAA TGC TGT CCA CCG
His Phe Pro Arg Ala Cys Val Ser Ser Lys Asn Leu Met Glu Lys Glu Cys Cys Pro Pro
             10                                          20

80              90             100             110             120             130
TGG AGC GGG ACA GGA GTC TGT GGC CAG CTT TCA GGC AGA GGT TCC TGT CAG AAT ATC CTT
Trp Ser Gly Thr Gly Val Cys Gly Gln Leu Ser Gly Arg Gly Ser Cys Gln Asn Ile Leu
             30                                          40

140             150             160             170             180             190
CTG TCC AAT GCA CCA CTT GGG CCT CAA TTT CCC TTC ACA GGG GTG GAT GAC CGG GAG TCG
Leu Ser Asn Ala Pro Leu Gly Pro Gln Phe Pro Phe Thr Gly Val Asp Asp Arg Glu Ser
             50                                          60

200             210             220             230             240             250
TGG CCT TCC GTC TTT TAT AAT AGG ACC TGC AGT GCT CTT GGC AAC TTC ATG GGA TTC AAC
Trp Pro Ser Val Phe Tyr Asn Arg Thr Cys Gln Cys Ser Gly Asn Phe Met Gly Phe Asn
             70                                          80

260             270             280             290             300             310
TGT GGA AAC TGC AAG TTT GGC TTT TGG GGA CCA AAC TGC ACA GAG AGA CGA CTC TTG GTG
Cys Gly Asn Cys Lys Phe Gly Phe Trp Gly Pro Asn Cys Thr Glu Arg Arg Leu Leu Val
             90                                         100

320             330             340             350             360             370
AGA AGA AAC ATC TTC GAT TTG AGT GCC CCA GAG AAG GAC AAA TTT TTT GCC TAC CTC ACT
Arg Arg Asn Ile Phe Asp Leu Ser Ala Pro Glu Lys Asp Lys Phe Phe Ala Tyr Leu Thr
            110                                         120

380             390             400             410             420             430
TTA GCA AAG CAT ACC ATC AGC TCA GAC TAT GTC ATC CCC ATA GGG ACC TAT GGC CAA ATG
Leu Ala Lys His Thr Ile Ser Ser Asp Tyr Val Ile Pro Ile Gly Thr Tyr Gly Gln Met
            130                                         140

440             450             460             470             480             490
AAA AAT GGA TCA ACA CCC ATG TTT AAC GAC ATC AAT ATT TAT GAC CTC TTT GTC TGG ATG
Lys Asn Gly Ser Thr Pro Met Phe Asn Asp Ile Asn Ile Tyr Asp Leu Phe Val Trp Met
            150                                         160
```

CAT TAT TAT GTG TCA ATG GAT GCA CTG CTT GGG GGA TAT GAA ATC TGG AGA GAC ATT GAT
His Tyr Tyr Val Ser Met Asp Ala Leu Leu Gly Gly Tyr Glu Ile Trp Arg Asp Ile Asp
            170                                     180

560           570           580           590          600           610

TTT GCC CAT GAA GCA CCA GCT TTT CTG CCT TGG CAT AGA CTC TTC TTG TTG CGG TGG GAA
Phe Ala His Glu Ala Pro Ala Phe Leu Pro Trp His Arg Leu Phe Leu Leu Arg Trp Glu
            190                                     200

620           630           640           650          660           670

CAA GAA ATC CAG AAG CTG ACA GGA GAT GAA AAC TTC ACT ATT CCA TAT TGG GAC TGG CGG
Gln Glu Ile Gln Lys Leu Thr Gly Asp Glu Asn Phe Thr Ile Pro Tyr Trp Asp Trp Arg
            210                                     220

680           690           700           710          720           730

GAT GCA GAA AAG TGT GAC ATT TGC ACA GAT GAG TAC ATG GGA GGT CAG CAC CCC ACA AAT
Asp Ala Glu Lys Cys Asp Ile Cys Thr Asp Glu Tyr Met Gly Gly Gln His Pro Thr Asn
            230                                     240

740           750           760           770          780           790

CCT AAC TTA CTC AGC CCA GCA TCA TTC TTC TCC TCT TGG CAG ATT GTC TGT AGC CGA TTG
Pro Asn Leu Leu Ser Pro Ala Ser Phe Phe Ser Ser Trp Gln Ile Val Cys Ser Arg Leu
            250                                     260

800           810           820           830          840           850

GAG GAG TAC AAC AGC CAT CAG TCT TTA TGC AAT GGA ACG CCC GAG GGA CCT TTA CGG CGT
Glu Glu Tyr Asn Ser His Gln Ser Leu Cys Asn Gly Thr Pro Glu Gly Pro Leu Arg Arg
            270                                     280

860           870           880           890          900           910

AAT CCT GGA AAC CAT GAC AAA TCC ACA ACC CCA AGG CTC CCC TCT TCA GCT GAT GTA GAA
Asn Pro Gly Asn His Asp Lys Ser Thr Thr Pro Arg Leu Pro Ser Ser Ala Asp Val Glu
            290                                     300

920           930           940           950          960           970

TTT TGC CTG AGT TTG ACC CAA TAT GAA TCT GGT TCC ATG GAT AAA GCT GCC AAT TTC AGC
Phe Cys Leu Ser Leu Thr Gln Tyr Glu Ser Gly Ser Met Asp Lys Ala Ala Asn Phe Ser
            310                                     320

980           990          1000          1010         1020          1030

TTT AGA AAT ACA CTG GAA GGA TTT GCT AGT CCA CTT ACT GGG ATA GCG GAT GCC TCT CAA
Phe Arg Asn Thr Leu Glu Gly Phe Ala Ser Pro Leu Thr Gly Ile Ala Asp Ala Ser Gln
            330                                     340
```

FIGURE 6B

| 1040 | 1050 | 1060 | 1070 | 1080 | 1090 |

AGC AGC ATG CAC AAT GCC TTG CAC ATC TAT ATG AAT GGA CAT GTC CCA GGT ACA GGA TCT
Ser Ser Met His Asn Ala Leu His Ile Tyr Met Asn Gly His Val Pro Gly Thr Gly Ser
            350                                      360

| 1100 | 1110 | 1120 | 1130 | 1140 | 1150 |

GCC AAC GAT CCT ATC TTC CTT CTT CAC CAT GCA TTT GTT GAC AGT ATT TTT GAG CAG TGG
Ala Asn Asp Pro Ile Phe Leu Leu His His Ala Phe Val Asp Ser Ile Phe Glu Gln Trp
         370                                    380

| 1160 | 1170 | 1180 | 1190 | 1200 | 1210 |

CTC CAA AGG CAC CGT CCT CTT CAA GAA GTT TAT CCA GAA GCC AAT GCA CCC ATT GGA CAT
Leu Gln Arg His Arg Pro Leu Gln Glu Val Tyr Pro Glu Ala Asn Ala Pro Ile Gly His
         390                               400

| 1220 | 1230 | 1240 | 1250 | 1260 | 1270 |

AAC CGG GAA TCC TAC ATG GTT CCT TTT ATA CCA CTG TAC AGA AAT GGT GAT TTC TTT ATT
Asn Arg Glu Ser Tyr Met Val Pro Phe Ile Pro Leu Tyr Arg Asn Gly Asp Phe Phe Ile
         410                               420

| 1280 | 1290 | 1300 | 1310 | 1320 | 1330 |

TCA TCC AAA GAT CTG GGC TAT GAC TAT AGC TAT CTA CAA GAT TCA GAC CCA GAC TCT TTT
Ser Ser Lys Asp Leu Gly Tyr Asp Tyr Ser Tyr Leu Gln Asp Ser Asp Pro Asp Ser Phe
         430                               440

| 1340 | 1350 | 1360 | 1370 | 1380 | 1390 |

CAA GAC TAC ATT AAG TCC TAT TTG GAA CAA GCG AGT CGG ATC TGG TCA TGG CTC CTT GGG
Gln Asp Tyr Ile Lys Ser Tyr Leu Glu Gln Ala Ser Arg Ile Trp Ser Trp Leu Leu Gly
         450                               460

| 1400 | 1410 | 1420 | 1430 | 1440 | 1450 |

GCG GCG ATG GTA GGG GCC GTC CTC ACT GCC CTG CTG GCA GGG CCT GTG AGC TTG CTG TGT
Ala Ala Met Val Gly Ala Val Leu Thr Ala Leu Leu Ala Gly Pro Val Ser Leu Leu Cys
         470                               480

| 1460 | 1470 | 1480 | 1490 | 1500 | 1510 |

CGT CAC AAG AGA AAG CAG CTT CCT GAA GAA AAG CAG CCA CTC CTC ATG GAG AAA GAA GGA
Arg His Lys Arg Lys Gln Leu Pro Glu Glu Lys Gln Pro Leu Leu Met Glu Lys Glu Gly
         490                               500

| 1520 | 1530 | 1540 | 1550 | 1560 | 1570 |

TTA CCA CAG CTT GTA TCA GAG CCA TTT ATA AAA GGC TTA GGC AAT AGA GTA GGG CCA AAA
Leu Pro Gln Leu Val Ser Glu Pro Phe Ile Lys Gly Leu Gly Asn Arg Val Gly Pro Lys
         510                               520

FIGURE 6C

| 1580 | 1590 | 1600 | 1610 | 1620 | 1630 |

AGC CCT GAC CTC ACT CTA ACT CAA AGT AAT GTC CAG GTT CCA GAG AAT ATC TGC TGG TAT
Ser Pro Asp Leu Thr Leu Thr Gln Ser Asn Val Gln Val Pro Glu Asn Ile Cys Trp Tyr
                530                                      540

| 1640 | 1650 | 1660 | 1670 | 1680 | 1690 |

TTT CTG TAA AGA CCA TTT GCA AAA TTG TAA CCT AAT ACA AAG TGT AGC CTT CTT CCA ACT
Phe Leu ---

| 1700 | 1710 | 1720 | 1730 | 1740 | 1750 |

CAG GTA GAA CAC ACC TGT CTT TGT CTT GCT GTT TTC ACT CAG CCC TTT TAA CAT TTT CCC

| 1760 | 1770 | 1780 | 1790 | 1800 | 1810 |

CTA AGC CCA TAT GTC TAA GGA AAG GAT GCT ATT TGG TAA TGA GGA ACT GTT ATT TGT ATG

| 1820 | 1830 | 1840 |

TGA ATT AAA AGT GCT CTT AGG AAT TC

FIGURE 6D

# A CDNA CLONE FOR HUMAN TYROSINASE

BACKGROUND OF THE INVENTION

Human tyrosinase is an essential enzyme which regulates the production of melanin, a group of brown or black pigments in the skin and eyes of humans. The lack of a human tyrosinase gene in usable form has greatly limited medical research in the field of albinism, and other medical and nonmedical applications relating to the control of pigment production in human melanocyte cells. This invention relates to the discovery of the cDNA gene which expresses human tyrosinase. When the cDNA is fused to an expression vector, the cDNA is useful to produce pure tyrosinase. When used as a cDNA probe the DNA is useful in the production or the control of production of human melanin. As a cDNA probe the cDNA gene is useful for genetic analysis of human albinism and melanotic and amelanotic melanoma, and also prenatal diagnosis of albinism.

There has been a minimum of research on the genetic control of melanin formation because of the lack of availability of suitable nucleic acid probe (gene sequence). cDNA for human tyrosinase is a key material for the study. The material will serve to understand why some melanoma cells lose the expression of tyrosinase gene and become more invasive. Differences in tyrosinase expression in cancer cells make it possible that the gene probe can be used in understanding and as a marker for malignancy. Understanding of the regulation of melanin biosynthesis will lead to the development of a rational chemotherapy of human melanoma because the intermediate substances of melanin are known to be toxic to pigment cells. Deletion of genes around albino locus (tyrosinase structural gene) becomes lethal in mice. The cDNA probe will open up a new research area to identify genes causing lethal effect in mouse embryo.

SUMMARY OF THE PRESENT INVENTION

The present invention resulted when a λ gt11 cDNA library of normal human melanocytes were screened with antibodies directed against purified hamster tyrosinase. Sixteen independent clones which gave a positive signal were isolated from $5 \times 10^5$ independent plaques. cDNA inserts of 13 clones among the 16 candidates cross-hybridized with each other, indicating that they were from related mRNA species. mRNA homologous to a representative cDNA λ mel 34 was expressed specifically in melanocytes, detecting an approximately 2.4 kb mRNA species of human melanocytes. The nucleotide sequence of the three overlapping cDNA inserts spanning 1.88 kb was determined and an amino acid sequence was deduced. The human tyrosinase is composed of 548 amino acids with a molecular weight of 62,160 excluding a hydrophobic signal peptide. Mouse genomic DNA blot analysis revealed that the gene for λ mel 34 was deleted in albino mouse homozygous for the deletion at and around the albino locus on chromosome 7. It is concluded that λ mel 34 contained cDNA encoding human tyrosinase. Moreover, the cDNA gene for human tyrosinase was recovered from the λ mel 34 and can be used for many purposes including the production of pure human tyrosinase.

In addition, the three clones of the 11 not represented by λ mel 34 are represented by λ mel 17-1. The gene for λ mel 17-1 cDNA was not mapped at the albino locus, detected single hybridizing restriction fragment in human and mouse DNA, and was highly conserved from mouse to human. The abundance of λ mel 17-1 cRNA paralleled the melanin content in human and mouse melanocytes. The expression of λ mel 17-1 cRNA was elevated after stimulation of mouse and human melanoma cells with MSH or/and IBMX, and U-V light (such as suntan). This was also closely correlated with the elevation of melanin content. The fact that the λ mel 17-1 gene is conserved evolutionarily indicates that the molecule encoded by the λ 17-1 has biologically important functions. The expression of that gene is controlled by hormones (MSH) or U-V light and positively correlated with the melanin content. These data indicate that the gene is involved in melanin biosynthesis in addition to tyrosinase. Current studies suggest that λ mel 17-1 gene product act on melanin biosynthesis's pathway distal to tyrosinase.

It is a primary object of the present invention to provide a new and improved cDNA gene which expresses human tyrosinase.

It is another object of the present invention to identify a new and improved cDNA gene which expresses human tyrosinase by its nucleotide sequence.

It is still another object of the present invention to teach that the cDNA from bacteriophage λ mel 34 may be used as a probe for the production or control of production of human melanin.

It is another object of the present invention to teach that the cDNA gene contained in the λ mel 34 is useful as a probe for genetic analysis of human albinism and melanotic and amelanotic melanoma, and also for prenatal diagnostics for albinism.

It is another object of the present invention to teach that the cDNA gene contained in λ mel 17-1 is useful as a probe for detecting the change in the degree of melanization of normal human melanocytes and melanoma cells.

BRIEF DESCRIPTION OF THE FIGURES

FIGS. 6A, 6B, 6C and 6D together are a table showing the nucleotide sequence of cDNA encoding human tyrosinase and its deduced amino acid sequence.

DETAILED DESCRIPTION OF THE INVENTION

As used herein the following abbreviations are used: Dopa, 3,4-dihydroxyphenylalanine; MSH, melanocyte stimulating hormone; TPA, 12-O-tetradecanoyl-phorbol-13-acetate; IBMX, isobutylmethylxanthine; TBS, 50 m M Tris HCL, pH 8.0, 0.15M NaCl; IPTG, isopropyl-beta-D-thiogalactopyranoside; PMSF, phenylmethylsolfonyl fluoride; PBS, 0.01M sodium phosphate, pH 7.4, 0.15M NaCl; SDS, sodium dodecyl sulfate; PAGE, polyacrylamide gel electrophoresis; SSC, 0.3M sodium chloride, 0.03M sodium citrate; Denhardt, 0.02% Ficoli, 0.02% polyvinylpyrrolidone, 0.02% bovine serum albumin.

Described herein is the isolation of a cDNA clone for human tyrosinase. Since human tyrosinase has not been sequenced, the following properties of the cDNA lead us to conclude that the mRNA homologous to λ mel 34 cDNA encodes authentic human tyrosinase: (1) the protein encoded by the cDNA binds to antityrosinase antibodies; (2) the mRNA corresponding to the cDNA (cRNA) is expressed in melanocytes but not in human neuroblastoma, lymphocytes, fibroblasts or hepatoma cells; (3) the molecular weight of protein encoded by λ mel 34 and λ mel 34-related cDNA clones is in good agreement with the reported size of de novo form of human tyrosinase (Hermann, W. P. and Uhlenbruck, G. (1975) Arch. Dermatol. Res. 254, 275–280.); and (4) the mouse gene corresponding to λ 34 cDNA is mapped at the albino locus of the mouse chromosome 7.

The availability of tyrosinase cDNA will open up a way to investigate the cis-acting regulatory sequence responsible for melanocyte-specific gene expression and the molecular genetic basis of human albinism and the related genetic disorders such as herein discussed (Witkop, C. J., Jr. (1984) In Clinics in Dermatology Vol. 2 (1), pp 70–98, J. B. Lippincott Co., U.S.A.). There are several varieties of human albinism (Witkop. C. J. Jr., Quevodo, W., Jr. and Fitzpatrick, T. B. (1983) In the Metabolic Basis of Inherited Disease. pp 301–346 (Stanbury, J. B., Wyngarden, J. B., Fredrickson, D. S., Goldstein, J. L., Brown, M. S., eds) McGraw-Hill, New York; King, R. A. and Witkop, C. J., Jr. (1976) Nature 263, 69–71; King, R. A. and Witkop, C. J., Jr. (1977) Am. J. Human Genet. 29, 164–168; King, R. A., Olds, D. P., and Witkop, C. J., Jr. (1978) J. Invest, Dermatol. 71, 136–139; King, R. A. and Olds, D. P. (1981) J. Invest. Dermatol. 77, 201–204), and in some of them a normal level of hair bulb tyrosinase can be measured. It may be possible, using the cDNA probe, to determine which of the differences are related to mutations in the tyrosinase structural gene and which may be due to mutations which affect synthesis of melanosomes, packaging of enzyme into melanosomes, or degradation of the enzyme. In conjunction with the accumulated genetic information on various mouse mutants affecting coat and eye color, the cDNA probe may be used to classify the molecular genetic nature of the mutations. There are strong indications for the existence of regulatory factors encoded near the mouse albino locus which appear to control various genes that map on other chromosomes, such as liver-specific enzymes and serum proteins (Gluecksohn-Waelsch, S. (1979) Cell 16, 225–237; Schmid, N. Muller, G., Schutz, G. and Gluecksohn-Waelsch, S. (1985) Proc. Natl. Acad. Sci. USA 82, 2866–2869; Loose, D. S., Schaw, P. A., Krauter, K. S., Robinson, C., Englard, S. Hanson, R. W. and Gluecksohn-Waelsch, S. (1986) Pro. Catl. Acad. Sci. USA, 83, 5184–5188). Since λ mel 34 detects the albino locus in mice this can be a starting material to identify such transacting regulatory genes in mice.

Posession of the cDNA probe for tyrosinase will allow further study of the regulation of tyrosinase synthesis by cAMP, MSH, and other hormones. In those cases where mRNA for tyrosinase is increased or decreased, a direct quantitation of mRNA can be made.

Tyrosinase's (EC 1.14.18.1) are copper containing enzymes that catalyze the conversion of tyrosine to dopa to dopaquinone, and thence to melanin (Mason, H. S. (1948) J. Biol. Chem. 172, 83–99). Several of the mammalian enzymes have been shown to be glycoproteins and to contain sialic acid residues (Miyazaki, K. and Ohtaki, N. (1975) Arch. Derm, Forsch. 252, 211–216; Hermann, W. P. and Uhlenbruck, G. (1975) Arch. Dermatol. Res. 254, 275–280; Nishioka, K. (1978) Eur. J. Biochem. 85, 137–146). There are multiple sizes of tyrosinases in all mammalian species which have been studied. These may be caused by differing contents of carbohydrate and as a result of the actions of difference structural genes.

Tyrosinase is an important factor in the development of pigmentation. Oculocutaneous albinism, a group of autosomal recessive diseases in humans (Witkop, C. J., Jr. Quevedo, W., Jr. and Fitzpatrick, T. B. (1983) In the Metabolic Basis of Inherited Disease. pp 301–346 (Stanbury, J. B., Wyngarden, J. B., Fredrickson, D. S., Goldstein, J. L., Brown, M. S., eds) McGraw-Hill, New York) and animals, is characterized by reduced or no melanin in skin and eye. However, some people with the condition have as much tyrosinase activity as fully pigmented individuals (King, R. A. and Witkop, C. J., Jr. (1976) Nature 263, 69–71; King, R. A. and Witkop, C. J., Jr. (1977) Am. J. Human Genet. 29, 164–168; King, R. A., Olds, D. P., and Witkop, C. J., Jr. (1978) J. Invest. Dermatol. 71, 136–139). The albino (C) locus in mice has been mapped to chromosome 7 (Coleman, D. E. (1962) Arch. Biochem. Biophys. 69, 562–568; Gluecksohn-Waelsch, S. (1979) Cell 16, 225–237).

Studies on the regulation of tyrosinase have focused on the role of MSH in humans and in whole animals (Lerner, A. B. and McGuire, J. S. (1961) Nature 189, 176–179; Pomerantz, S. H. and Chuang, L. (1971) Endocrinol. 87 301–310; Lee, T. H., Lee, M. S., and Lu, M. X. (1972) Endocrinol. 91 . 1180–1188) and in normal and malignant melanocytes in culture (Halaban, R., Pomerantz, S. H., Marshall, S., Lambert, D. T. and Lerner, A. B. (1983) J. Cell Biol. 97, 480–488; Halaban, R., Pomerantz, S. H., Marshall, S. and Lerner, A. B. (1984) Arch. Biochem. Biophys. 230, 383–387). The later studies showed that MSH increased the rate of synthesis of tyrosinase.

A nucleic acid probe for tyrosinase would be valuable for a thorough study of the regulation of tyrosinase, the molecular genetic basis of human albinism and of various mouse mutants affecting coat and eye color, and the relationship between melanocyte differentiation and tyrosinase gene expression. Described here is the isolation of a cDNA clone for human tyrosinase which maps at or near the mouse C locus.

EXPERIMENTAL PROCEDURES

Cell culture

Normal human melanocytes were cultured from newborn foreskin by a method modified by us (Halaban, R. and Alfano, F. D. (1984) In Vitro 20, 447–450) from that of Eisinger and Marko (Eisinger, M. and Marko, O. (1982) Proc. Natl. Acad. Sci. USA 79, 2018–2022). The cells were grown in Ham's F-10 medium (American Biorganics) containing 8% fetal calf serum (Gibco), 8% Nu-serum (Collaborative Research), 100 ug/ml penicillin, 200 units/mil streptomycin (Gibco), 85 nM TPA (Consolidated Midland Corp.), 0.1 mM IBMX (Sigma) and 2.5 nM cholera toxin (List Biological Laboratories). In the most recent experiments cholera toxin was replaced by human placental extract (20 ug/ml) (Halaban, F. Ghosh, S., Duray, P., Kirkwood, J. M. and Lerner, A. B. (1986) J. Invest. Dermatol. 87, 95–101).

Melanoma and neuroblastoma cells were grown in Ham's F-10 medium supplemented with penicillin, streptomycin, 8% fetal calf serum and 8% Nu-serum. The melanoma cell line used was human metastatic LG (melanotic) cultured by us from the brain (Halaban, et al. supra). The human neuroblastoma SK-N-SH (Ross, R. A. and Biedler, J. L. (1985) Adv. Neuroblast. Res. pp. 249–259. (Evans, A. E., D'Ansio. G. J., Seeser, R. C., eds). Raven Press, New York) was received from Dr. J. L. Biedler, Sloan Kettering Institute, New York, N.Y. The murine neuroblastoma cell line NIE115 was obtained from Dr. X. O. Breakefield, Harvard University, Cambridge, Mass.

To radiolabel proteins of normal melanocytes the cultures were first incubated for 24 hours in methionine-free medium (American Biorganics) supplemented with TPA, cholera toxin, 3% dialyzed calf serum and [$^{35}$S] methionine (Amersham) (100 uCi/ml, 1390 Ci/mole). The cells were lysed with 0.5 ml PBS containing 1% NP-40 (Sigma) and 0.1 mM PMSF (Sigma) and agitated on a vortex mixer. The lysate was centrifuged at 15,000 g for 15 minutes, the specific radioactivity in protein of the supernatant was determined in 5 ul aliquots, and the supernatant was used as a crude radiolabeled tyrosinase preparation.

Preparation of cDNA libraries of normal human melanocytes

Total cellular RNA or normal human melanocytes was prepared by guanidine isothiocyanate-cesiumchloride gradient centrifugation essentially as described by Chirgwin et al. (Chirgwin, J. M., Przybyla, A. E., MacDonald, R. J. and Rutter, W. J. (1978) Biochemistry 18, 5194–5299). Poly(A)+ RNA was selected by chromatography on a column of oligo d(T) cellulose (Aviv, H. and Leder, P. (1972) Proc. Natl. Acad. Sci. USA 69 . 1408–1412) (Collaborative Research Type 2). Double stranded cDNAs were prepared from poly (A)+ mRNA as previously described (Schwarzbauer, J. E., Tamkun, J. W., Lemischka, I. R. and Hynes, R. O. (1983) Cell 35, 421–431; Land, H., Grez, J., Hauser, H., Lindenmaier, W. and Schutz, G. (1981) Nucleic Acids Res. 9, 2251–2261). The cDNA was EcoRI-methylated at internal EcoRI restriction sites with EcoRI methylase (New England Biolabs) (Maniatis, T., Hardison, R. C., Lacy, E., Lauer, J., O'Connel, C., Quon, D., Sim, G. K. and Efstratiadis, A. (1978) Cell, 687–701) to prevent degradation at the step of EcoRI-linker addition. EcoRI linkers were ligated to both ends of cDNA molecules which were blunt-ended by treating with S1 nuclease followed by E. coli DNA polymerase 1 large fragments. The cDNAs were fractionated on 1 ml columns of Bio-gel A-150m (Bio Rad) and enriched for those composed of over 400 base pairs. λ gtll DNA (Young, R. A., and Davis, R. W. (1983) Proc. Natl. Acad. Sci. USA 80, 1194–1198) was digested with EcoRI and treated with bacterial alkaline phosphatase (Worthington, 0.2 u/ug DNA) at 65° for 1 hour to decrease self-ligation. The cDNAs were inserted into the unique EcoRI site of λ gtll cloning vector. The recombinant phage DNA was packaged in vitro as described by Grosveld et al (Grosveld, F. G., Dahl, H. H. M., deBoer, E. and Flavell, R. A. (1981) Gene 13, 227–237). The λ gtll library contained 1.7×10$^6$ independent plaques. A pilot experiment showed that 88% of the plaques contained cDNA inserts based on beta-galactosidase activity. The λ gtll cDNA library was amplified in E. coli strain Y1088 (Huynh, T. V., Young, R. A. and Davis, R. W. (1984) In DNA CLoning: A Practical Approach, vol. 1, pp. 49078 (D. Glover, ed.) IRL Press, Arlington, Va.) as a host and stored at 4° C.

Screening for the gene products of the λ gtll melanocyte cDNA library with antityrosinase antibodies The immunobiological screening as carried out as described by Young and Davis (Young, R. A. et al. supra). Recombinant phages were absorbed to bacterial strain Y1090 and plated on 150 mm L-agar plates. The plates were incubated at 42° C. for 3 hours. Nitrocellulose filters, soaked in 50 mM IPTG were placed on the plates and incubated for 3 hours at 37° C. The filters were removed and washed in TBS twice and treated with 20% fetal calf serum in TBS for one hour. The filters were washed with TBS twice and TBS+0.1% NP-40 once. The filters were incubated with antityrosinase antibodies (available from Dr. Seymour H. Pomerantz, Department of Biological Chemistry, University of Maryland School of Medicine, Baltimore, Md. 21201) in TBS plus 20% fetal calf serum in a sealed plastic bag overnight at 4° C. At the same time another set of IPTG-treated filters were overlayed on plaques and incubated overnight at 37° C. to obtain duplicate filters. The second set of filters were processed the same way as the first set of filters except that the binding period to antityrosinase antibody was two hours at room temperature. Both sets of filters were washed extensively with TBS and TBS plus 0.1% NP-40 at room temperature. [$^{125}$I] protein A (New England Nuclear) was diluted to 1×10$^5$ cpm/ml in TBS and incubated with the filters for 1 hour at room terperature with shaking. Filters were washed three times with TBS and blotted dry and autoradiographed with intensifying screen at −70° C. The duplicate filters were compared to search for positive signals in both filters.

Detection of fusion protein

The lysogens of the recombinant and nonrecombinant λ gtll were prepared employing E. coli strain Y1089 (Huynh, T. V., Young, R. A. and Davis, R. W. (1984) In DNA Cloning: A Practical Approach, vol. 1, pp. 49–78 (D. Glover, ed.) IRL Press, Arlington, Va.). The lysogens were grown at 32° C. until they reached logarithmic phase (OD$_{600}$=0.5). Lytic replication was then induced by a temperature shift (42° C., 20 min) and cultures were incubated at 37° for 3 hours in the presence of IPTG at a final concentration of 1 mM. The bacterial cells were suspended in a buffer containing 10 mM Tris HCL pH 7.4, 0.15M NaCl, 1 mM PMSF, 50 ug/ml DNase 1 (Sigma) and 50 ug/ml of RHase (Boehringer Manneheim). The soluble fractions of the sonicated bacterial cell suspension were run on a 6% polyacrylamide gel (Laemmli, U. K. (1970) Nature 227, 680–685).

Immunoprecipitation and competition with antityrosinase antibodies

For competition experiments, antityrosinase antibodies were incubated on ice overnight with bacterial lysates prepared from E. coli Y1089 lysogens of λ gtll or λ gtll plus cDNA. [$^{35}$S] methionine labeled extract from black foreskin melanocytes (6×10$^6$ cpm in protein/assay) was added to each assay tube, followed 15 minutes later by 10 ul of IgGSorb (The Enzyme Center, Inc., 250 mg/ml). At the end of 15 minutes incubation with IgGSorb, the cell lysates were centrifuged at 13,000 g for 0.5 minutes, the pellet of IgGSorb with bound immune complexes washed 3 times with PBS plus 0.1% NP-40 and once with PBS. The immune complexes were eluted from the IgGSorb with sample buffer (Laemmli supra) and subjected to polyacrylamide gel electrophoresis followed by fluorography of the gels as described before (Halaban et al. supra). For quantitation of labeled protein, gel slices were taken from relevant radioactive bands, rehydrated with 25 ul water and digested overnight with 5% Protosol (National Diagnostics) in Econofluor (NEN) at 37° C., and the radioactivity counted.

Northern blot analysis

Poly(A)+ RNA from normal human melanocytes, melanoma cells, neuroblastoma cell lines, HL-60 (human promyelocytic leukemia cell line) and HepG-2 (human hepatocarcinoma cell line) was fractionated on a 1.2% formaldehyde denaturing gel (Thomas, P. S. (1980) Proc. Natl. Acad. Sci. USA 77, 5201-5205) and transferred to a nitrocellulose filter or Gene Screen plus membrane (NEN). [$^{32}$P] labeled cDNA probes were hybridized overnight to the filter at 42° C. in 5 times concentrated SSC, 50% formaldehyde, 50 mM sodium phosphate buffer pH 6.8, 10% dextran sulfate, Denhardt, 0.1% SDS and 250 ug/ml denatured salmon sperm DNA. Filters were then washed three times for 5 minutes each in 2 times concentrated SSC and 0.1% SDS at room temperature and three times at 42° C. in 5 times concentrated SSC, 5% formaldehyde, 50 mM sodium phosphate buffer pH 6.8, 10% dextran sulfate, Denhardt, 0.1% SDS and 250 ug/ml denatured salmon sperm DNA. Filters were then washed three times for 5 minutes each in 2 times concentrated SSC and 0.1% SDS at room temperature and three times at 42° C. in 0.1 concentrated SSC and 0.1% SDS. The filters were autoradiographed at −70° C. When a Northern blot of Gene Screen plus was used multiple times for hybridization, the previous probe was removed by treating the membrane in 10 mM Tris-HCl pH 7.0 and 0.2% SDS at 85° C. for 1 hour.

Genomic Southern blot analysis

High molecular weight DNAs of murine embryos homozygous for the lethal deletion $c^{3H}/c^{3H}$, heterozygous for the deletion, ($c^{3H}/c^{ch}$) and of normal homozygote chinchilla ($c^{ch}/c^{ch}$), were prepared as described previously (Grass-Bellard, M., Oudet, P. and Chambon, P. (1973) Eur. J. Biochem. 36, 32-38). $c^{3H}/c^{3H}$ and $c^{3H}/c^{ch}$ mice were obtained from Dr. Gluecksohn-Waelsch at the Albert Einstein College of Medicine and may be purchased from Johnson Laboratories, Inc., Bar Harbor, Me. Restriction endonuclease digests of DNA were electrophoresed in a 0.8% agarose gel at 4° C. The gel was denatured with 0.5M NaOH/1M NaCl and neutralized with 1M Tris HCl pH 8.0/1M NaCl. The DNA in the gel was transferred to Gene Screen plus as described by Southern (Southern, E. (1975) J. Mol. Biol. 98, 503-517). For a low stringent hybridization and washing the blot was hybridized with the [$^{32}$P] labeled cDNA in 6 times concentrated SSC, 5 times concentrated Denhardt solution, 0.5% SDS and 100 ug/ml denatured salmon sperm DNA for 24 hours at 58° C. The filters were then washed two times at room temperature for 10 minutes each in 2 times concentrated SSC, 0.1% SDS and two times at 55° C. for 30 minutes each in 2 times concentrated SSC and 0.1% SDS, and two times at room temperature for 30 minutes in SSC.

Isolation of λ phage DNA and preparation of inserted DNA

Recombinant phage DNA was prepared as described by Davis et al (Davis, R. W., Botstein, D. and Roth, J. R. (1980) Advanced Bacterial Genetics, pp. 106-107, Cold Spring Harbor Laboratory, Cold Spring Harbor, N.Y.). The recombinant DNA was cut with EcoRI, and the cDNA inserts were separated from λ phage arms by 1% agarose gel. The cDNA bands were cut out of the agarose gels, run on 5% polyacrylamide gels, eluted from the gels in 0.1 SSC, and precipitated with ethanol.

DNA sequencing

DNA restriction fragments, subcloned in M13 vectors (Messing, J., Crea, R. and Seeburg, P. H. (1981) Nucleic Acids Res. 9 . 309-322), were sequenced by the dideoxy chain termination technique (Sanger, F., Nicklen, S. and Coulson, A. R. (1977) Proc. Natl. Acad. Sci. USA 74, 5463-5467), with modifications made to accommodate 2'-deoxy-adenosine 5'-[alpha-[$^{35}$S]thio]-triphosphate (Biggin, M., Gibson, T. and Hung, G. (1983) Proc. Natl. Acad. Sci. USA 80, 3963-3965).

RESULTS

Isolation of cDNA clones from human melanocyte λ gt11 library which react with antityrosinase antibodies A λ gt11 cDNA library of normal human melanocytes was screened with rabbit antityrosinase antibodies raised against purified hamster tyrosinase. The antityrosinase antibodies have been shown to cross react with human, murine and avian tyrosinase (Halaban, R. et al. (1983) supra; Halaban, R. et al. (1984) supra). The antibodies immunoprecipitated newly-synthesized as well as processed tyrosinase and were abosrbed completely by extracts from melanocytes but not from fibroblasts.

Figure 1:
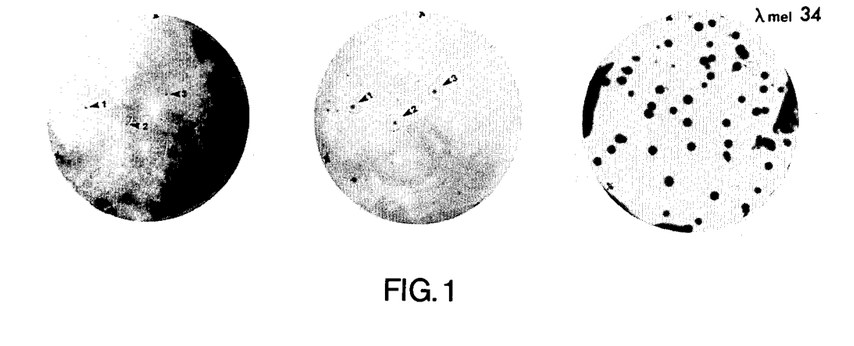
FIG. 1 in three panels depicts the isolation of hyman tyrosinase cDNA by antibody screening.

Initial screening of approximately 500,000 recombinant phages with rabbit antityrosinase antibodies identified sixteen independent clones which gave positive signals. These clones were consistently reactive with antityrosinase antibodies but not with nonimmune rabbit serum during several rounds of screening for plaque-purification. FIG. 1 shows an example of duplicate primary (a and b) and the third round (c) of screening. FIG. 1 depicts the isolation of human tyrosinase cDNA by antibody screening. A λ gt11 cDNA library of human melanocytes was screened with antityrosinase antibody directed against hamster tyrosinase and $^{125}$I-labeled protein A (NEN). Filter panels a and b represent duplicate filters prepared from the same plate of λ gt11 cDNA library. Signals in filter a (1, 2 and 3) correspond to those in filter b. It was found that the duplicate screening method was helpful in discriminating false-positive signals. Filter panel c shows the third round of screening during the plaque purification of λ mel 34.

Recombinant phage DNAs from each of the 16 clones were prepared, digested with EcoRI to excise the cDNA insert and fractionated on a 1% agarose gel. Sizes of the cDNA inserts varied from 0.2 to 1.6 kb. The longest cDNA insert (§1.6) kb) from λ mel 34 was hybridized to 12 other cDNA inserts and shared an overlapping restriction pattern. The other three cDNA inserts were not related to the thirteen cDNA clones. The thirteen cDNA inserts were partially overlapping but none of them were the same clone. The fact that overlapping sequences were found repeatedly indicates that the antibody reacted to the peptides encoded by specific sequences present in the cDNA species. The 1.6 kb cDNA insert of λ mel 34 was subcloned into PBR322 to yield pmel 34 and used to amplify the cDNA insert.

mRNA homologous to λ mel 34 is expressed preferentially in melanocytes

Figure 2:
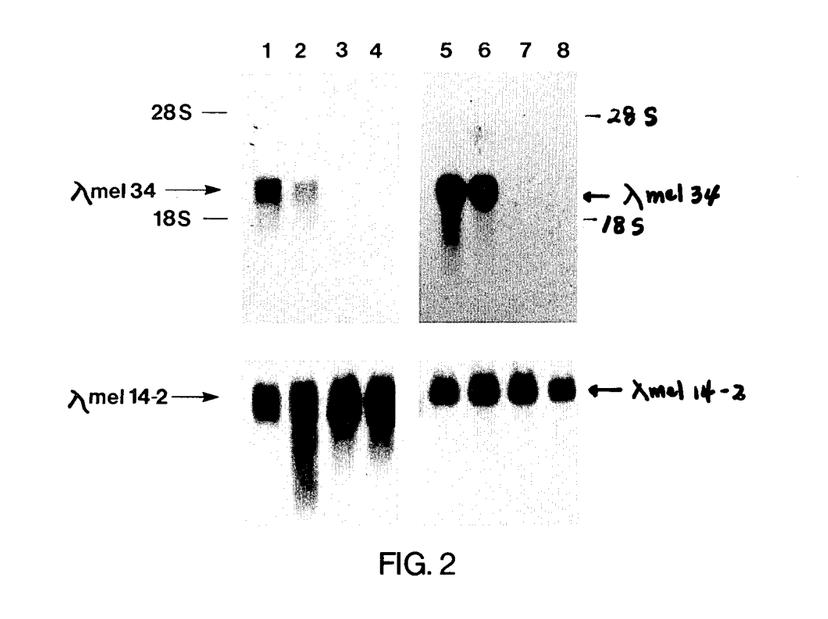
FIG. 2 is a Northern blot analysis of poly(A)+RNA derived from normal melanocyte, human melanotic melanoma (LC), HePG-2, HL-60, human and mouse neuroblastoma.

Tyrosinase is presumed to be expressed only in pigment cells. To examine whether λ mel 34 homologous mRNA is expressed only in melanocytes, Northern blot analysis of poly(A)+ mRNA from normal human melanocytes, human melanotic melanoma cells (LG), human neuroblastoma, murine neuroblastoma, HePG-2 (human hepatoma cell line) and HL-60 (human promyelocytic leukemia cell line) was performed using [$^{32}$P] labeled mel 34 cDNA as a probe. FIG. 2 is a Northern blot analysis of poly (A)+ RNA (a) of normal human melanocyte (lane 1), LG (lane 2), HepG-2 (lane 3) and HL-60 (lane 4) cells, and 10 ug of poly(A)+ RNA (b) of normal human melanocyte (lane 5), LG (lane 6), human neuroblastoma (lane 7) and mouse neuroblastoma cells (lane 8) were fractionated on 1.2% formaldehyde denaturing agarose gel, blotted and hybridized with [$^{32}$P]-labeled mel 34 cDNA (upper arrow). The same filter was used to hybridize to [$^{32}$]-labeled λ mel 14-2 (bottom arrow) to show that each lane contained RNA as indicated above and the RNA was relatively intact. λ mel 14-2 is a cDNA clone which was isolated from human melanocyte cDNA library and has been used as a control probe because the corresponding RNA was detectable in smilar amounts from all human and mouse cells tested. As shown in FIGS. 2a and b, λ mel 34 hybridized to 21S (~2.4 kb) mRNA species of normal human melanocytes and human melanotic melanoma cells but not to HePG-2, HL-60, human or murine neuroblastoma mRNA. A cDNA fragment (λ mel 14-2) is isolated from melanocyte cDNA library was used as a control probe to show that a similar amount of mRNA was loaded in each lane (FIG. 2a and b). In addition, λ mel 34 cRNA was not expressed in other human and mouse fibroblasts and lymphocytes (data not shown). Further studies showed that λ mel 34 cRNA expression was correlated with tyrosinase activity and melanin content in human melanoma cells. Amelanotic melanoma cells (no or little melanin-containing cells) expressed far less λ mel 34 cRNA than normal or melanotic melanoma cells.

Fusion protein of λ mel 34-related clone, λ mel 16

Figure 3:
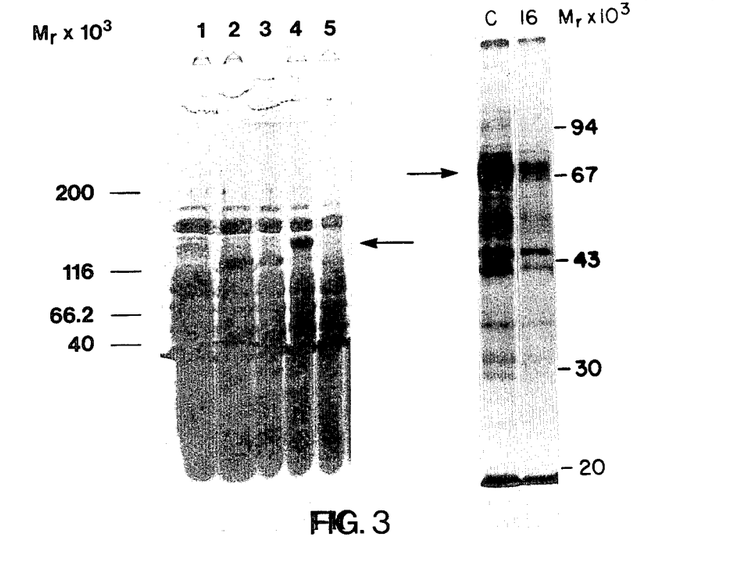
FIG. 3 is a SDS PAGE presentation of the detection of λ mel 16 beta-galactosidase tyrosinase fusion protein.

To characterize the fusion protein further, lysogens of λ gtll and λ mel 16 (§0.7 kb), which were isolated at an earlier stage of this work and which cross hybridized to λ mel 34, were prepared and analyzed by 6% SDS PAGE and competitive immunoprecipitation assay. FIG. 3 depicts the detection of λ mel 16 beta-galactosidase-tyrosinase fusion protein. Panel a: Bacterial lysates were prepared from the lysogens Y1089/λ gtll (lanes 1 and 2), Y1089/λ mel 19 (lane 3) and Y1089/λ mel 16 (lanes 4 and 5) following inactivation of the temperature-sensitive repressor at 42° C. and subsequent incubation in the absence (lanes 1 and 5) or presence (lanes 2, 3, and 4) of IPTG. λ mel 16 and λ mel 19 were λ mel 34-related clones which were isolated in the early phase of this work. Reduced samples were run on a 6% SDS-polyacrylamide gel, and stained with Coomassi-blue. The IPTG-dependent production of beta-galactosidase (lane 2) and ~140 kd λ mel 16 fusion protein (lane 5, arrow) was noted. Protein sizes in kilodaltons are marked left. Panel b: The lysate of λ mel 16 or λ gtll lysogen was used to compete with metabolically labeled human melanocyte cell extract for antityrosinase antibodies. Constant amounts of lysates of λ gtll or λ mel 16 lysogens (~2×10$^7$ cells in 100 ul volume) were incubated with 5 ul of 1:100 dilute of antityrosinase antibodies. The absorbed antibodies were used to immunoprecipitate the [$^{35}$S] labeled human melanocyte extract (6×10$^6$ cpm in protein/tube). The eluted immune complexes were analyzed on an 8.5% polyacrylamide gel. There were 3,780 cpm in control lane and 1,186 cpm in λ mel 16 lane, in the gel slices taken from the tyrosinase bands (arrow). As shown in FIG. 3a, a fusion protein was produced in Y1089 (λ mel 16) which had a relative size of approximately 140,000 daltons. This was approximately 25,000 daltons larger than that of E. coli beta-glactosidase. This indicates that the cDNA in λ mel 16 is fused to beta-galactosidase gene in frame, producing an almost entire protein encoded by the cDNA. Synthesis of both beta-galactosidase and the fusion protein was dependent on induction with IPTG. The lysate of λ mel 16 lysogen was used to compete with metabolically labeled melanocyte cell extract for antityrosinase antibodies. A typical experiment is shown in FIG. 3B. When bacterial lysates of λ gtll or λ mel 16 lysogens (approximately 2×10$^7$ cells in 100 ul volume) were incubated with 1 ul of 1:100 dilution of antityrosinase antibodies, approximately 70% of antityrosinase activity was absorbed by λ mel 16 lysate compared with λ gtll control lysates based upon the intensity of tyrosinase bands and radioactivity count of the gel slices taken from tyrosinase bands. Since the antibody preparation is poly-clonal the λ mel 16 encoding protein, containing only a partial sequence of tyrosinase, may not bind all of the antityrosinase antibodies.

Gene for λ mel 34 is deleted in chromosome of albino locus-deleted mouse, c$^{3H}$/c$^{3H}$ Earlier studies showed that the skin of mice carrying the albino locus deleted mutant c$^{3H}$/c$^{3H}$ has no tyrosinase activity (Gluecksohn-Waelsch, S. (1979) supra). However, the tyrosinase activity levels in the skin of mice heterozygous to lethal albino deletions and chinchilla (c$^{3H}$/c$^{ch}$) were shown to be intermediate between normal (c$^{ch}$/c$^{ch}$) and mutant (c$^{3H}$/c$^{3H}$) homozygotes, confirming that the albino locus of mice encodes the structural gene of tyrosinase.

Because the deletion around the albino locus in c$^{3H}$/c$^{3H}$ mice is large enough to cover the tyrosinase gene (Gluecsolh-Waelsch, S. (1979) supra), authentic tyrosinase cDNA should not detect any band (c$^{3H}$/c$^{3H}$) mice DNA but should detect hybridizing bands of half normal intensity of the homozygote (c$^{ch}$/c$^{ch}$) in the heterozygous litter mate (c$^{3H}$/c$^{ch}$). To test this prediction, genomic DNAs from (c$^{3H}$/c$^{3H}$), (c$^{3H}$/c$^{ch}$) and (c$^{ch}$/c$^{ch}$) were digested with EcoRI and the fragments were separated on 0.8% agarose gel, transferred to Gene Screen Plus, and probed with the [$^{32}$P]-labeled λ mel 34 cDNA. After autoradiograph, the λ mel 34 cDNA probe was stripped and the same filter was probed with [$^{32}$P]-labeled λ mel 17-1 cDNA. λ mel 17-1 is one of the three cDNA clones among the initial 16 clones which is unrelated to λ mel 34.

Figure 4:
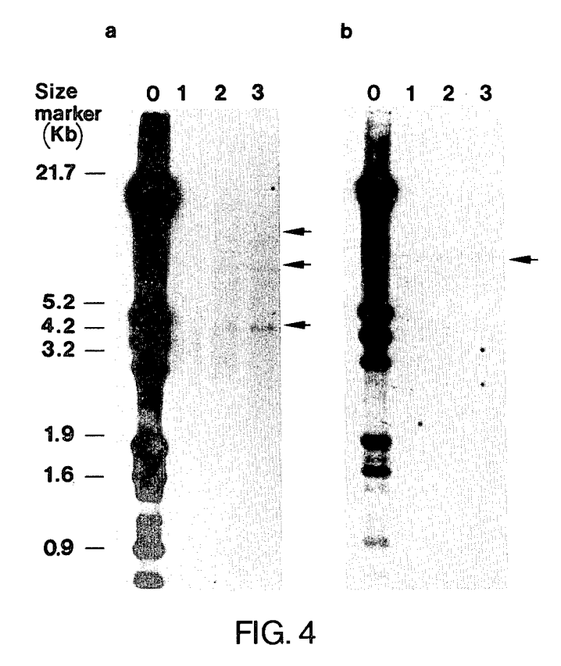
FIG. 4 is a Southern blot analysis of genomic DNA of deletion homozygous ($c^{3H}/c^{3H}$) in newborn mice.

As shown in FIG. 4a, λ mel 34 detected three hybridizing fragments whose sizes were approximately 4.5 kb, 12.0 kb and 14.5 kb in (c$^{ch}$/c$^{ch}$) DNA. According to the hybridization conditions the mouse tyrosinase gene. Those three bands were also detected in (c$^{3H}$/c$^{ch}$) at approximately half the intensity of that with (c$^{ch}$/c$^{ch}$)

DNA. No hybridizing fragment was detected in ($c^{3H}/c^{3H}$) DNA even after longer exposure. Therefore, the mouse genes whose sequences are homologous to cDNA contained in λ mel 34 are located at or near the albino locus. FIG. 4 is a Southern blot analysis of genomic DNA of deletion homozygous ($c^{3H}/c^{3H}$) (lane 1), ($c^{3H}/c^{ch}$) (lane 2) and ($c^{ch}/c^{ch}$) (lane 3) mice was digested with EcoRI, run on a 0.8% agarose gel, transferred to Gene Screen Plus and hybridized to λ mel 34 cDNA (a). The same filter was probed with mel 17-1 after stripping λ mel 34 cDNA probe (b). λ mel 17-1 is one of the sixteen clones which we initially isolated and proved not to be related to λ mel 34. Size markers are Hind III fragments of λ phage DNA. As shown in FIG. 4b, λ mel 17-1, one of the three other clones we initially isolated, detected a 13.0 kb band in all three mouse DNAs at relatively similar intensities. Therefore λ mel 17-1 clone is unrelated to the albino locus.

Nucleotide sequence analysis

Figure 5:
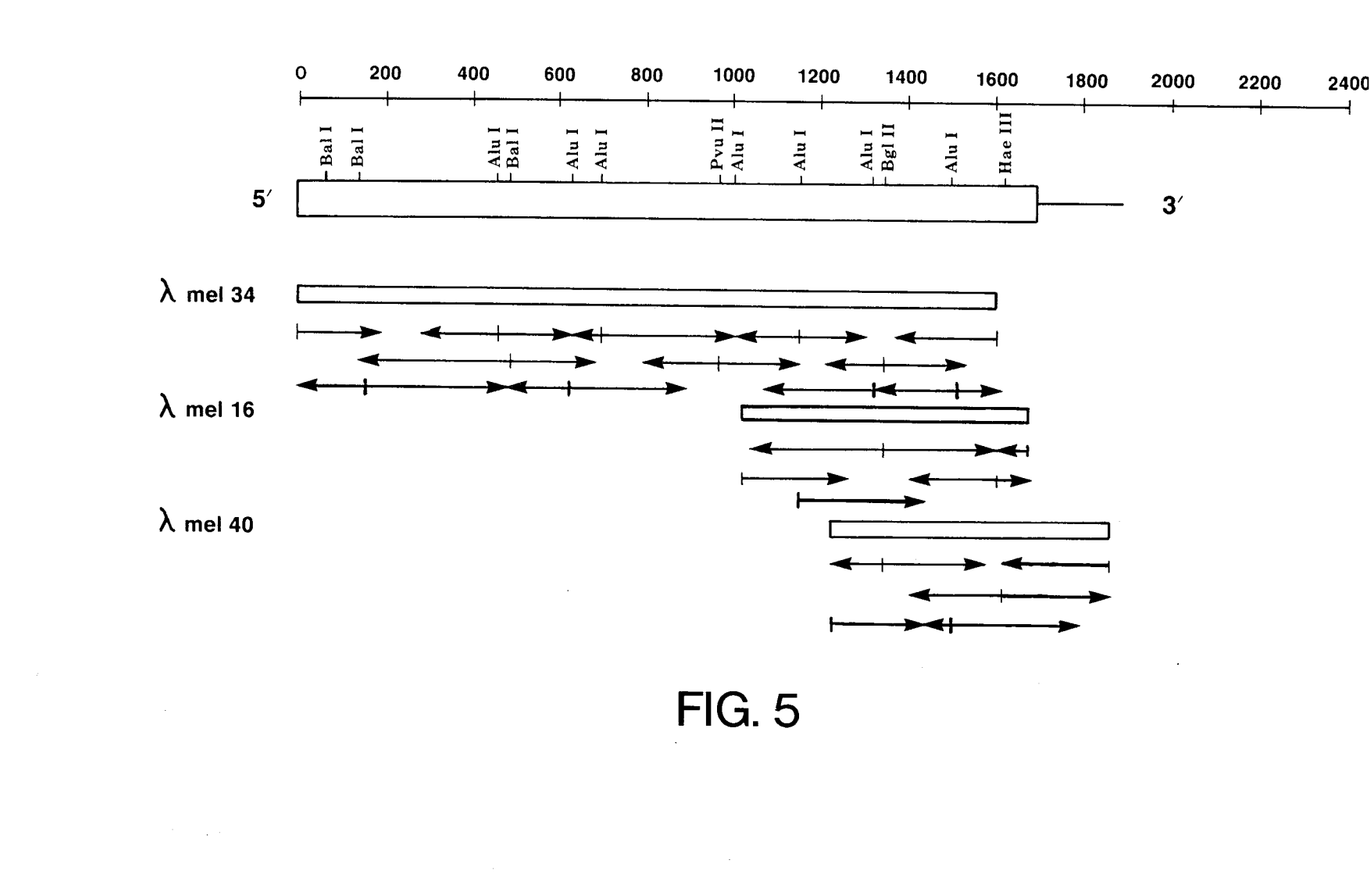
FIG. 5 is a Partial Restriction map and sequencing strategy for human tyrosinase cDNA.
Figure 6D:
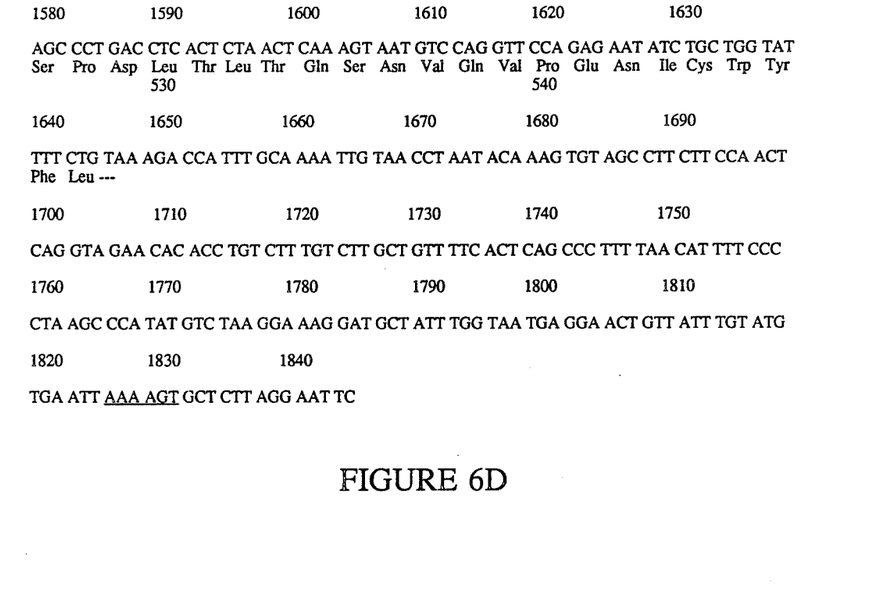

The entire nucleotide sequence of three overlapping cDNA clones (λ mel 34, λ mel 16 and λ mel 40) was determined according to the strategy shown in FIG. 5. FIG. 5 shows partial restriction map and sequencing strategy for human tyrosinase cDNA. The protein-coding region is indicated by an open box and a putative signal peptide is represented by a shaded box. Horizontal arrows under the 3 inserts show the direction and extent of sequencing used to generate the sequence presented in FIG. 6. Restriction sites used for sequencing are indicated. The scale at the top indicates the nucleotide number. The 5'sides of the other 10 clones were also sequenced. The nucleotide sequence of tyrosinase cDNA revealed a single long open reading frame, beginning with the first nucleotide after the EcoRI linker. This open reading frame is in frame with the lacZ gene of the λ gtll vector. We found that the other 10 clones are also fused in frame with lacZ gene. This property was helpful in assigning the open reading frame even though the cDNAs did not start the first ATG codon. This reading frame codes for a polypeptide of 560 amino acids with a molecular weight of 63,549 (FIG. 6). FIG. 6 lists nucleotide sequence of cDNA encoding human tyrosinase and its deduced amino acid sequence. The nucleotide sequence of message strand is numbered in the 5' to 3' direction. Numbers above each line refer to nucleotide position. Nucleotide residue 1 is the T of the first codon TTC of putative mature protein, and the nucleotides of a portion of putative signal peptide are indicated by negative numbers. The predicted amino acid sequence is shown below the nucleotide sequence. Numbers below the amino acid sequence refer to amino acid position, beginning with the amino-terminal residue of the mature tyrosinase. The preceding residues of a portion of putative signal peptide are indicated by negative numbers. Potential glycosylation signals and potential polyadenylation signals are underlined. - - - indicates stop codon. The codon specifying carboxy-terminal leucine is followed by the translation termination codon TAA (Nucleotide residue, 1645–1647). No nucleotide differences were observed among the three cDNA clones except that they differ in length. The 3'-untranslated sequence determined from λ mel 34, λ mel 16 and λ mel 40 does not extend as far as the poly(A)+ tail. However λ mel 40 contains a potential polyadenylation signal of AT-TAAA (Goeddel, D. V., Leung, D. W., Dull, T. J., Gross, M., Lawn, R. M., McCandliss, R., Seeburg, P. H., Ullrich, A., Yelverton, E. and Gray, P. W. (1981) Nature 290, 20–26) (nucleotide residues, 1822–1827).

Amino acid sequence

The sequence of the first eleven amino acid residues exhibits a feature characteristic of the signal peptide of secretary and membrane-associated proteins (Blobel, G. and Dobberstein, B. (1975) J. Cell Biol. 67, 852–862), which mainly contains hydrophobic amino acide (9 out of 11) and terminate with serine having a small side chain (Steiner, D. F., Quinn, P. S., Chan, S. J., Marsh, J. and Tager, H. S. (1980) Ann. N.Y. Acad. Sci. 343, 1–16) (FIG. 6). Therefore, a possible site for cleavage of the signal peptide of putative tyrosinase precursor is after the serine residue at position 1 of phenylalanine (FIG. 6). This prepeptide is probably involved in the transfer of tyrosinase into the melanosome. Thus, mature tyrosinase is composed of 548 amino acids with a molecular weight of 62,160. As tyrosinase is a glycoprotein, we examined the possible N-glycosylation sites. There are five potential aspargine-linked glycosylation signals, Asn-X-Ser-S or Thr, where X is any amino acid except proline (Marshall, R. D. (1974) Biochem. Soc. Symp. 40, 17–26; Bause, E. (1983) Biochem. J. 209, 331–336). The possible glycosylation sites are the asparagine residues at positions 73, 98, 148, 217 and 324 as underlined in FIG. 6. Tyrosinases contain two copperatoms per enzyme molecule (Nishioka, K. (1978) Eur. J. Biochem. 85, 136–146; Lerch, K. (1976) FEBS Letters 69, 157–160). Therefore, we examined the possible copper-binding sites by comparison with human (Jabusch, J. R., Farb, D. L., Kerschensteiner, D. A. and Deutsch, H. F. (1980) Biochemistry 19, 2310–2316) and bovine (Richardson, J. S., Thomas, K. A., Rubin, B. H. and Richardson, D. C. (1975) Proc. Natl. Acad. Sci. USA 72, 1349–1353) superoxide dismutase. Crystallographic study of bovine superoxide dismutase (Richardson, J. S. et al. (1975) supra) has shown that His-44, His-46, and His-61 are ligands to copper. There are 15 histidine residues in the deduced amino acid sequence of human tyrosinase. Histidine residues at positions 350, 354, 360 and 377 showed a similar arrangement to bovine superoxide dismutase. By analyzing albino and normal human DNA using λ mel 34 as a probe the genetic defect of tyrosinase gene in human albinism will be established. The cDNA contained in λ mel 34 will be further used to analyze amniotic cell DNA of suspected individuals for prenatal diagnosis of albinism. The cDNA (λ mel 34) will be used to produce a pure human tyrosinase by recombinant DNA technology in bacteria. This will facilitate obtaining a large quantity of pure human tyrosinase. Obtaining a large quantity of pure human tyrosinase is essential to study of the three dimensional structure of the enzyme. Clarification of the tyrosinase structure will lead to establishment of the rationale for chemotherapy against malignant melanoma because presursors to melanin is toxic to melanotic melanoma cells.

To produce the tyrosinase in *E. coli*, λ mel 34 cDNA will be fused to an expression vector (Tac) which has Trp and 1 ac promoter together. Tac, the expression vector is available communally through suppliers such as U.S. Pharmacia, Inc. The construct will be expressed in *E. coli* strain MM294. Subsequently the tyrosinase will be purified by affinity column chromatography.

Subsequently it was found that the cDNA inserts of the three clones which were not related to λ mel 34 were cross-hybridized to each other and expressed specifically in melanocytes. This indicates that they were not isolated spuriously, rather that the protein encoded by the cDNAs were reactive to the antityrosinase antibody and had melanocyto-specific functions.

The representative clone λ mel 17-1 detected approximately 2.5 kb mRNA species in only melanocytes. The gene for λ mel 17-1 cDNA was not mapped at the albino locus, detected single hybridizing restriction fragment in human and mouse DNA, and was highly conserved from mouse to human. The abundance of λ mel 17-1 cRNA paralleled the melanin content in human and mouse melanocytes. The expression of λ mel 17-1 cRNA was elevated after stimulation of mouse and human melanoma cells with MSH or/and IBMX, and U-V light (such as suntan). This was also closely correlated with the elevation of melanin content. The fact that the λ mel 17-1 gene is conserved evolutionarily indicates that the molecule encoded by the λ mel 17-1 has biologically important functions. The expression of the gene is controlled by hormones (MSH) or U-V light and positively correlated with the melanin content. These data indicate that the gene is involved in melanin biosynthesis in addition to tyrosinase. Current studies suggest that λ mel 17-1 gene product act on melanin biosynthesis's pathway distal to tyrosinase.

The foregoing description has been directed to particular embodiments of the invention in accordance with the requirements of the Patent Statutes for the purposes of illustration and explanation. It will be apparant, however, to those skilled in this art that many modifications and changes will be possible without department from the scope and spirit of the invention. It is intended that the following claims be interpreted to embrace all such modifications.

Bacteriophage λ mel 34 cDNA has been deposited at the American Type Culture Collection under ATC No. 40265 and will be available after this Patent Application issues.

Bacteriophage λ mel 17-1 cDNA has been deposited at the American Type Culture Collection under ATC No. 40264 and will be available after this Patent Application issues.

I claim:

1. A cDNA gene that encodes for human tyrosinase.

2. A cDNA gene that encodes for human tyrosinase comprising a nucleotide sequence as shown in FIGS. 6A, 6B, 6C and 6D.

3. A bacteriophage vector for use in cloning human tyrosinase cDNA comprising a replicon identified as λ mel 34 cDNA deposited at the American Type Culture Collection at 12301 Parklawn Drive, Rockville, Md. 20852 under ATC No. 40265.

4. A method of making human tyrosinase comprising the steps of:
   a. fusing the lambda mel 34 cDNA encoding human tyrosinase to an expression vector wherein said cDNA is under the functional control of a promoter sequence;
   b. expressing tyrosinase in *E. coli;*
   c. purifying the resulting tyrosinase.

5. The cDNA for human tyrosinase comprising the cDNA recovered from the bacteriophage λ mel 34 cDNA which is deposited at the A.T.C. Collection under no. 40265.

6. A method of using the cDNA gene for human tyrosinase recovered from the λ mel 34 cDNA as deposited at the A.T.C. Collection under No. 40265 as a probe for genetic analysis of human albinism comprising the steps:
   (a) labeling said cDNA;
   (b) hybridizing said labeled cDNA with albino human genomic DNA; and
   (c) detecting the patterns of hybridization.

* * * * *